(12) United States Patent
Ard et al.

(10) Patent No.: US 8,352,283 B2
(45) Date of Patent: Jan. 8, 2013

(54) METHODS AND SYSTEMS FOR MINIMIZING COSTS OF DRUG PURCHASES

(75) Inventors: Teresa Ard, Fulshear, TX (US); Rick Burnett, Katy, TX (US); Kathy Chase, Prairie Village, TX (US); Alisa Goetz, Bellaire, TX (US); Joel McTopy, Sugar Land, TX (US); Kathy McTopy, Sugar Land, TX (US)

(73) Assignee: Cardinal Health Pharmacy Services, Houston, TX (US)

( * ) Notice: Subject to any disclaimer, the term of this patent is extended or adjusted under 35 U.S.C. 154(b) by 928 days.

(21) Appl. No.: 11/866,931

(22) Filed: Oct. 3, 2007

(65) Prior Publication Data

US 2009/0094051 A1    Apr. 9, 2009

(51) Int. Cl.
*G06Q 10/00* (2012.01)
*G06Q 50/00* (2012.01)

(52) U.S. Cl. .................................. 705/2; 705/3; 705/14

(58) Field of Classification Search .................. 705/2–4, 705/14

See application file for complete search history.

(56) References Cited

U.S. PATENT DOCUMENTS

| 6,978,286 | B2 * | 12/2005 | Francis et al. | 708/132 |
| 2001/0047299 | A1 * | 11/2001 | Brewer et al. | 705/14 |
| 2004/0024617 | A1 * | 2/2004 | Fralic | 705/2 |
| 2007/0162303 | A1 * | 7/2007 | Wiley et al. | 705/2 |
| 2008/0313103 | A1 * | 12/2008 | Burns et al. | 705/400 |

* cited by examiner

*Primary Examiner* — Michelle Le
(74) *Attorney, Agent, or Firm* — Arent Fox LLP (57) ABSTRACT

Drug purchases are evaluated according to available offers from drug manufacturers, based on the equivalent dosage regimens for similar drugs. Equivalent doses among drugs are calculated. Purchasing amounts of equivalent doses of drugs are reviewed. The costs of the equivalent doses of the drugs are compared, taking into account contractual price adjustments, such as discounts and rebates. Subsequent purchasing amounts of the drugs are determined, using results from the comparisons. The new purchasing amounts of the equivalent doses of the drugs are produced.

27 Claims, 9 Drawing Sheets

Customer Purchase Detail Upload

| NDC | Trade Name | Generic Name | Strength | Form | Size | Units | Package L Dollars |
|---|---|---|---|---|---|---|---|
| | 80/20 Product Movement Report | | | | | | |
| 00074610905 | ABBOKINASE | UROKINASE | 250MU | PWVL | 1 EA | 18 | $7,772.58 |
| 57665010141 | ABELCET | AMPHOTERICIN B LIPID COMLEX | 5MG/ML | SDV | 20 ML | 20 | $1,500.00 |
| 50924097601 | ACCU-CHEK INSTANTPLUS | DIABETIC SUPPLIES | NOT AVAILABLE | KIT | 1 | 15 | $2,255.10 |
| 00064100001 | ACCUZYME | PAPAIN/UREA | 650000U/GM-10% | OINT | 30 GM | 166 | $6,457.40 |
| 66220010703 | ACETADOTE | ACETYLCYSTEINE | 200MG/ML | SDPF | 4X30ML | 7 | $3,192.00 |
| 00406048462 | ACETAMINOPHEN W/CODEINE | CODEINE/ACETAMIN | 30-300MG | TABS | 100 EA | 85 | $857.65 |
| 51079016120 | ACETAMINOPHEN W/CODEINE | CODEINE/ACETAMIN | 30-300MG | TABS | 100 EA | 30 | $649.20 |
| 55339046001 | ACETAZOLAMINE SODIUM | ACETAZOLAMIDE SODIUM | 500MG | PWVL | 1 EA | 108 | $1,728.00 |
| 00517760425 | ACETYLCYSTEINE | ACETYLCYSTEINE | 200MG/ML | AMPS | 25X4ML | 79 | $1,975.00 |
| 00517750425 | ACETYLCYSTEINE | ACETYLCYSTEINE | 100MG/ML | AMPS | 25X4ML | 68 | $1,700.00 |
| 00574012074 | ACTIDOSE WITH SORBITOL | CHARCOAL/SORBITOL SOLUTION | 25GM | LIQD | 120ML | 148 | $1,388.24 |
| 50242008527 | ACTIVASE | ALTEPLASE | 100MG | PWVL | 1 EA | 16 | $45,215.42 |
| 50242004413 | ACTIVASE | ALTEPLASE | 50MG | PWVL | 1 EA | 7 | $9,941.92 |
| 00149047001 | ACTONEL | RISEDRONATE SODIUM | 30MG | TABS | 30 EA | 2 | $991.26 |
| 64764015104 | ACTOS | PIOGLITAZONE HCL | 15MG | TABS | 30 EA | 22 | $2,066.90 |
| 64764045125 | ACTOS | PIOGLITAZONE HCL | 45MG | TABS | 90 EA | 4 | $1,957.84 |
| 64764030115 | ACTOS | PIOGLITAZONE HCL | 30MG | TABS | 90 EA | 2 | $902.44 |
| 64764030114 | ACTOS | PIOGLITAZONE HCL | 30MG | TABS | 30 EA | 6 | $902.40 |
| 55390061210 | ACYCLOVIR SODIUM | ACYCLOVIR SODIUM | 500MG | PWVL | 10X1EA | 47 | $1,645.00 |
| 00085171603 | ADALAT CC | NIFEDIPINE | 60MG | TABS | 100 EA | 8 | $1,856.00 |

Figure 6

| Drug Name | Drug A | | | |
|---|---|---|---|---|
| Base Price Discount | 0% | | | |
| | Market Share (Tier) Discount | | | |
| Range % | % | | Discount % | Rebate % |
| 0% | to | 39.99% | 0.0% | 0.0% |
| 40% | to | 59.99% | 25.0% | 5.0% |
| 60% | to | 69.99% | 25.0% | 10.0% |
| 70% | to | 79.99% | 25.0% | 15.0% |
| 80% | to | 100.00% | 25.0% | 21.5% |
| 0% | to | 0.00% | 0.0% | 0.0% |

Contract Name:
Contract Terms: Jan 2004 - Dec 2007
Contract MS Mgmt Criteria: WAC
Market Basket

Figure 7

Customer Current State

| | | | | | amount purchased | | | | WAC per Each | Total WAC purchased | Total Current Rebate |
|---|---|---|---|---|---|---|---|---|---|---|---|
| Regimen A | Name | Dose | Pkg SZ | units/pkg | unit cost | Packages | units | Total $ purchased | | | |
| NDC | | | | | | | | | | | |
| 597007506 | DRUG 1 | 18MCG 6 | CAP W/DEV | 1 | $ 28.82 | 69 | 69 | $ 1,988.58 | $ 29.48 | $ 2,034.12 | |
| | | | | | | | | | | | |
| Regimen B | | Dose | Form | units/pkg | unit cost | Packages | units | Total $ purchased | WAC per Each | Total WAC purchased | Total Current Rebate |
| NDC | | | | | amount purchased | | | | | | |
| 597008717 | DRUG 2 | 17MCG | AER W/ADAP | 1 | $ 68.91 | 6 | 6 | $ 413.46 | $ 70.50 | $ 432.00 | |
| 597001314 | DRUG 3 | 14.7 GM | AER W/ADAP | 1 | 76.27 | 149 | 149 | $ 11,364.23 | $ 78.03 | $ 11,626.47 | |
| | | | | | | | | | | | |

METHODS AND SYSTEMS FOR MINIMIZING COSTS OF DRUG PURCHASES

TECHNICAL FIELD

The present disclosure relates to the purchasing of drugs by an organization, taking into account contract offers including discounts and rebates, among other things.

BACKGROUND

The relatively high cost of drugs is a growing concern for suppliers, health care providers, patients and insurance companies. Health care providers, such as hospitals, seek to provide the drugs they require at the lowest cost. Hospitals often serve as the intermediary sellers between drug manufacturing companies and hospital patients who may be considered the ultimate consumers. Hospitals are able to obtain lower prices from the drug manufacturers by purchasing in bulk. Drug manufacturers competing for the business often offer discounts based on purchasing amounts and relative use of their products. For example, a drug company might provide a 15% discount on a certain drug to treat a particular condition, as long as this drug comprises 75% of the total amount of drugs that the hospital uses to treat that condition (i.e., equivalent drugs). The contract terms can be relatively complex, making comparisons of purchasing scenarios difficult.

Consider the following example. Drug manufacturer 'A' offers drug 'X' at various prices for various different dosage quantities e.g., $7 for a 500 mg dose and $13 for a 1 g dose. Drug 'X' treats anemia, and drug manufacturer 'A' offers a 20% discount if a hospital purchases at least 60% of its anemia drugs from drug manufacturer 'A.' However, if a hospital purchases at least 80% of its anemia drugs from drug manufacturer 'A', the hospital is entitled to a 15% discount on all drugs purchased from drug manufacturer 'A' (not only drug 'X'), and will receive an additional rebate of 10% on all drug 'X' purchases. At the same time, drug manufacturer 'B' offers drug 'Y,' also an anemia drug, and is in competition with drug manufacturer 'A.' Drug manufacturer 'B' offers drug 'Y' at various prices for various different dosage quantities e.g., $5 for a 500 mg dose and $9 for a 1 g dose. Drug manufacturer 'B' offers a 15% discount if a hospital purchases at least 30% of its anemia drugs from drug manufacturer 'B.' However, if a hospital purchases at least 40% of its anemia drugs from drug manufacturer 'B', the hospital is entitled to a 20% discount on drug 'Y,' and will receive an additional rebate of 15% on all drug 'Y' purchases.

Hospitals must examine many variables in order to properly consider these offers and make the best purchasing decision. Hospitals normally examine the discounts and rebates, as well as other consequences of contracting with a drug manufacturer, and of failing to meet the requirements which make the hospital eligible for other discounts and rebates.

The complexity of a hospital's purchasing decisions is apparent, even from this simplified example. At present, hospitals employ a series of ad hoc spreadsheets in determining their drug purchases. These spreadsheets evaluate offers from drug manufacturers based on units purchased. They are cumbersome to use, because of the continually changing contract terms offered, such as changing discounts and rebates. Also, basing purchasing decisions on units purchased does not take into account how the drugs are actually used. For example, a 500 mg dose of drug 'X' may be therapeutically equivalent to a 1 mg dose of drug 'Y.' Hence, it would be misleading to compare the number of units of 500 mg of drug 'X' purchased to the number of units of 500 mg of drug 'Y' purchased, because twice as many units of drug 'Y' are needed to achieve the same therapeutic result. A calculation that compares total costs of purchase of drug 'X' and drug 'Y' based on the number of units purchased therefore does not provide the most accurate comparison.

SUMMARY

There is a need in the art for methods and systems that evaluate drug purchases according to the current offers from drug manufacturers, taking into account the equivalent dosage regimens for similar drugs, and to provide relative purchasing amounts of the similar drugs.

One method of the present disclosure, begins by determining doses for at least two drugs. Next, the purchasing amounts of the equivalent doses of the drugs are reviewed. The costs of the equivalent doses of the drugs are then compared, taking into account any contractual price adjustments, such as discounts and rebates. Following this, new purchasing amounts of the equivalent doses of the drugs are determined, using the results from the comparison in the previous step. Finally, the new purchasing amounts of the equivalent doses of the drugs are produced.

Additional features and advantages of the disclosure will be set forth in the description below, and in part will be apparent from the description, or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure. In the drawings:

FIG. 6 is a table showing a user's exemplary previous drug purchases.

DETAILED DESCRIPTION

It is contemplated that the subject matter described herein may be embodied in many forms. Accordingly, the embodiments described in detail below are the presently preferred embodiments, and are not to be considered as limitations.

The disclosed embodiments address, among other things, the evaluation of drug purchases.

Figure 1:
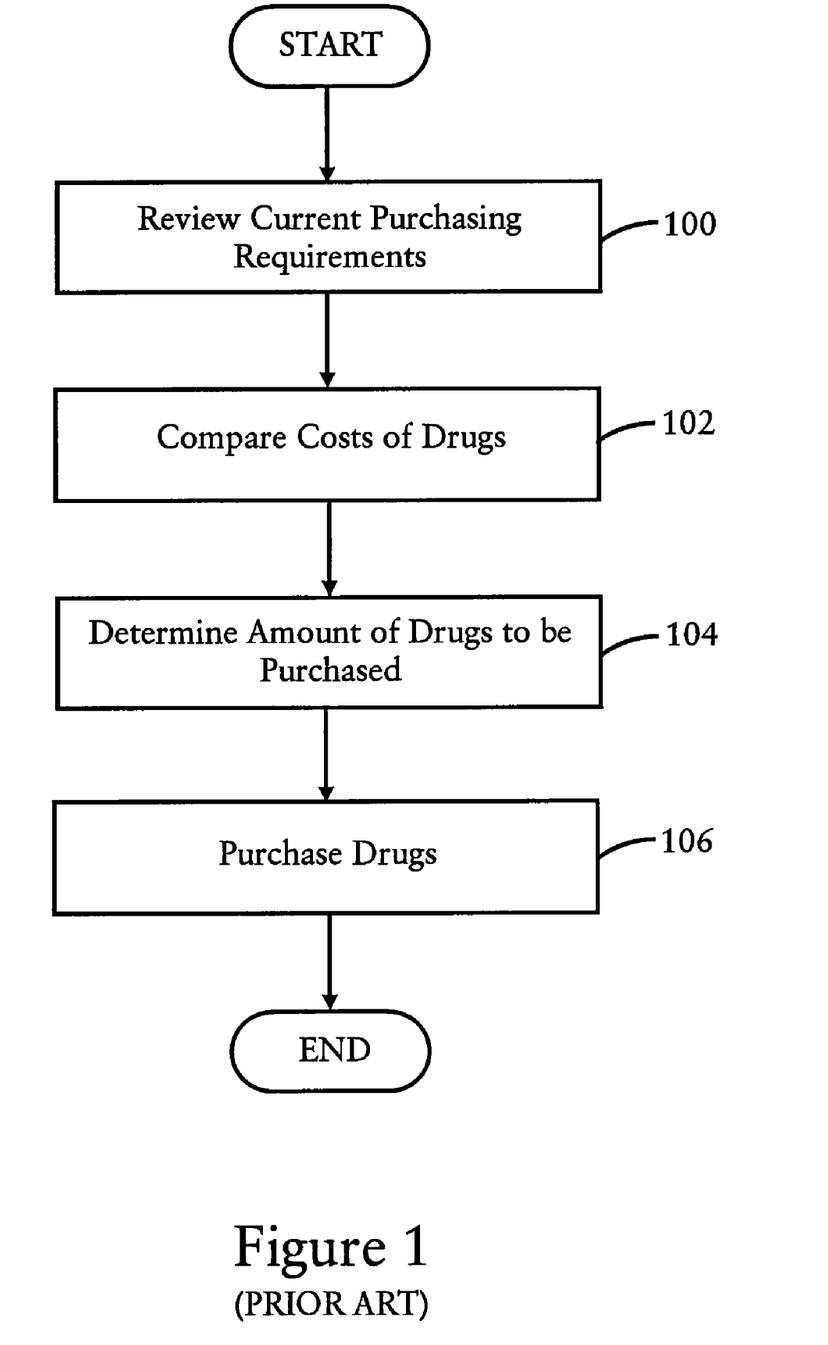
FIG. 1 is a flow chart diagram depicting existing methods for determining the amount of drugs to be purchased.

At present, as shown in FIG. 1, the current purchasing requirements are evaluated in step 100. This is essentially a determination of the usage of the drugs, and the contract requirements. The costs of drugs are then compared on a per unit basis in step 102. Thus, if drug 'X' and drug 'Y' are both used for the same therapeutic purpose, and cost $5 and $7 per gram respectively, then drug 'X' will be considered to have a cheaper base cost than drug 'Y.' The actual costs may differ once the different discounts and rebates are factored in. Based on the usage and comparison of costs, an amount of drugs to be purchased is determined in step 104. The drugs are then purchased in step 106.

There are a number of problems with the prior art evaluation method. One is that it fails to take into account differences in the therapeutic potency of similar drugs. Although both drug 'X' and drug 'Y' are used for the same purpose, double the amount of drug 'X' may be required to achieve the same effect as drug 'Y.' So the proper comparison in that example would then not be $5 for drug 'X' to $7 for drug 'Y,' but rather $10 for drug 'X' to $7 for drug 'Y.'

Figure 9:
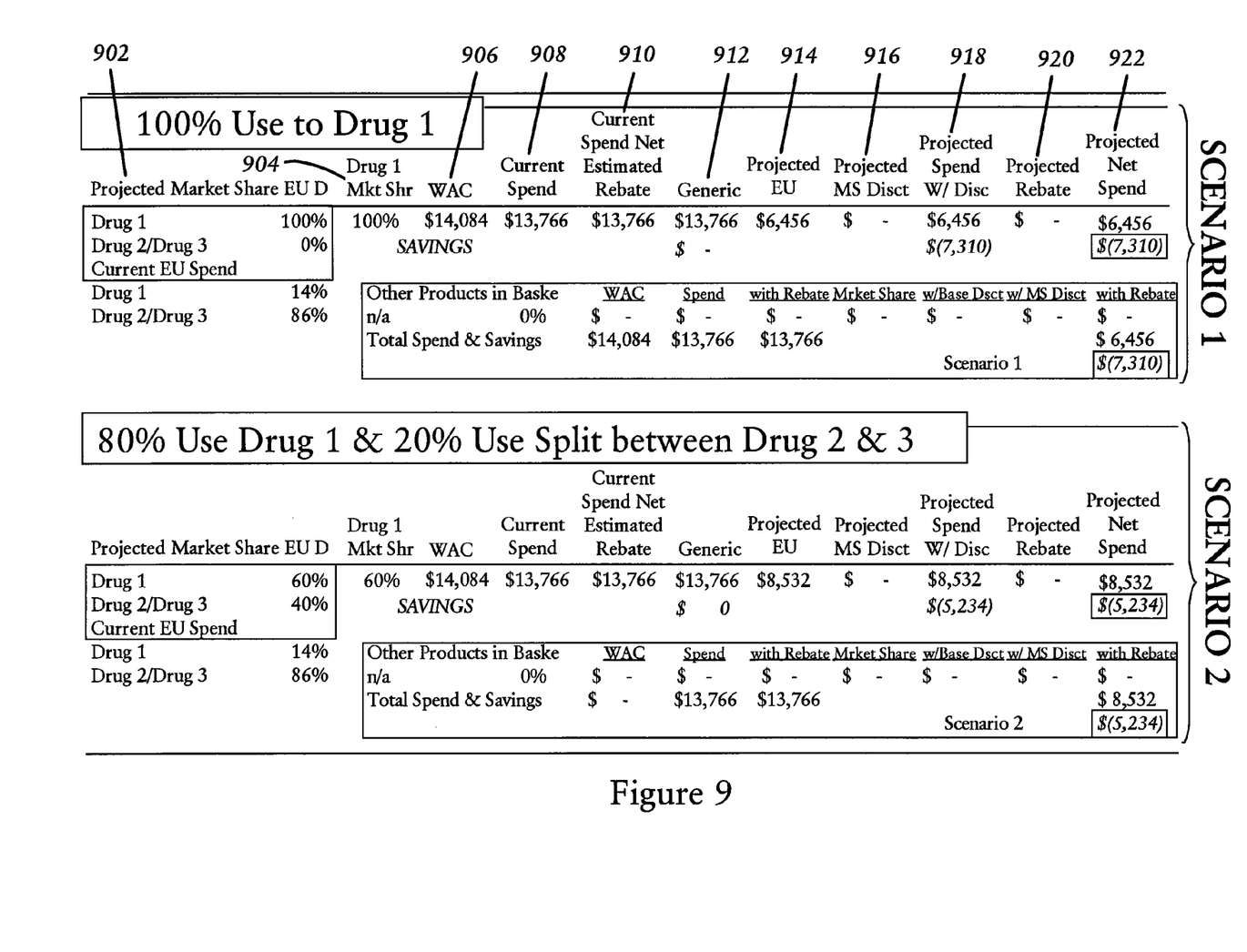
FIG. 9 shows two tables each displaying a separate exemplary purchasing scenario for comparison.

Another problem is that the method of FIG. 9 fails to consider the frequency of dosage. So, even though drug 'X' and drug 'Y' are used for the same purpose, drug 'X' may need to be administered three times a week, whereas drug 'Y' may only need to be administered twice a week. The proper comparison would then not be $5 for drug 'X' to $7 for drug 'Y,' but rather $15 for drug 'X' to $14 for drug 'Y.'

A further problem is that the present method fails to take into account the period over which treatment of the drug must be administered. Although drug 'X' and drug 'Y' have the same purpose, drug 'X' may require a treatment period of three weeks, whereas drug 'Y' may require a treatment period of four weeks. The proper comparison would then not be $5 for drug 'X' to $7 for drug 'Y,' but rather $15 for drug 'X' to $28 for drug 'Y.'

The present disclosure solves both of these problems, among other things, by comparing the cost of drugs based on therapeutically equivalent dose regimens. So, in the example above, where drug 'X' is half as effective as drug 'Y,' needs to be administered three times a week (as opposed to twice a week for drug 'Y'), and must be administered for a period of three weeks (as opposed to four weeks for drug 'Y') the proper equivalent unit ratio (for one month's use) between drug 'X' and drug 'Y' (X:Y) is: ($5×2×3×3): ($7×1×2×4), or $90: $56, i.e., $1.61: $1. Thus, comparing drug 'X' and drug 'Y' based on their equivalent dosage regimens, the price of drug 'X' is more than one and a half times that of drug 'Y' per month. This provides a more accurate price comparison than the $5:$7 ratio per gram, which would be used in the prior art. Thus the presently disclosed embodiments take into account how a drug is actually used when evaluating its cost, rather than merely comparing drug costs on a unit for unit basis. When the equivalent dosage regimen is accounted for, a unit is referred to as an equivalent dose unit, or simply an equivalent unit.

Figure 2:
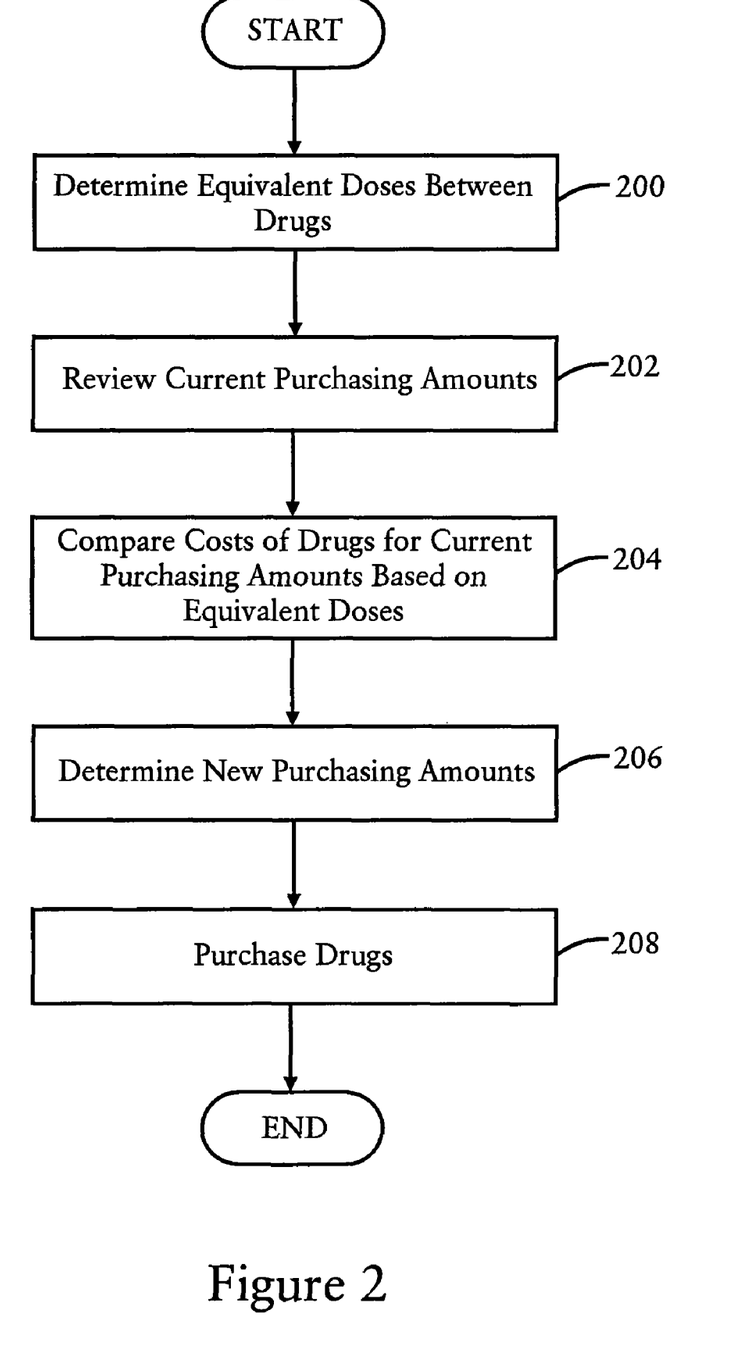
FIG. 2 is a flow chart diagram depicting a method of the present disclosure for determining the amount of drugs to be purchased.
Figure 4:
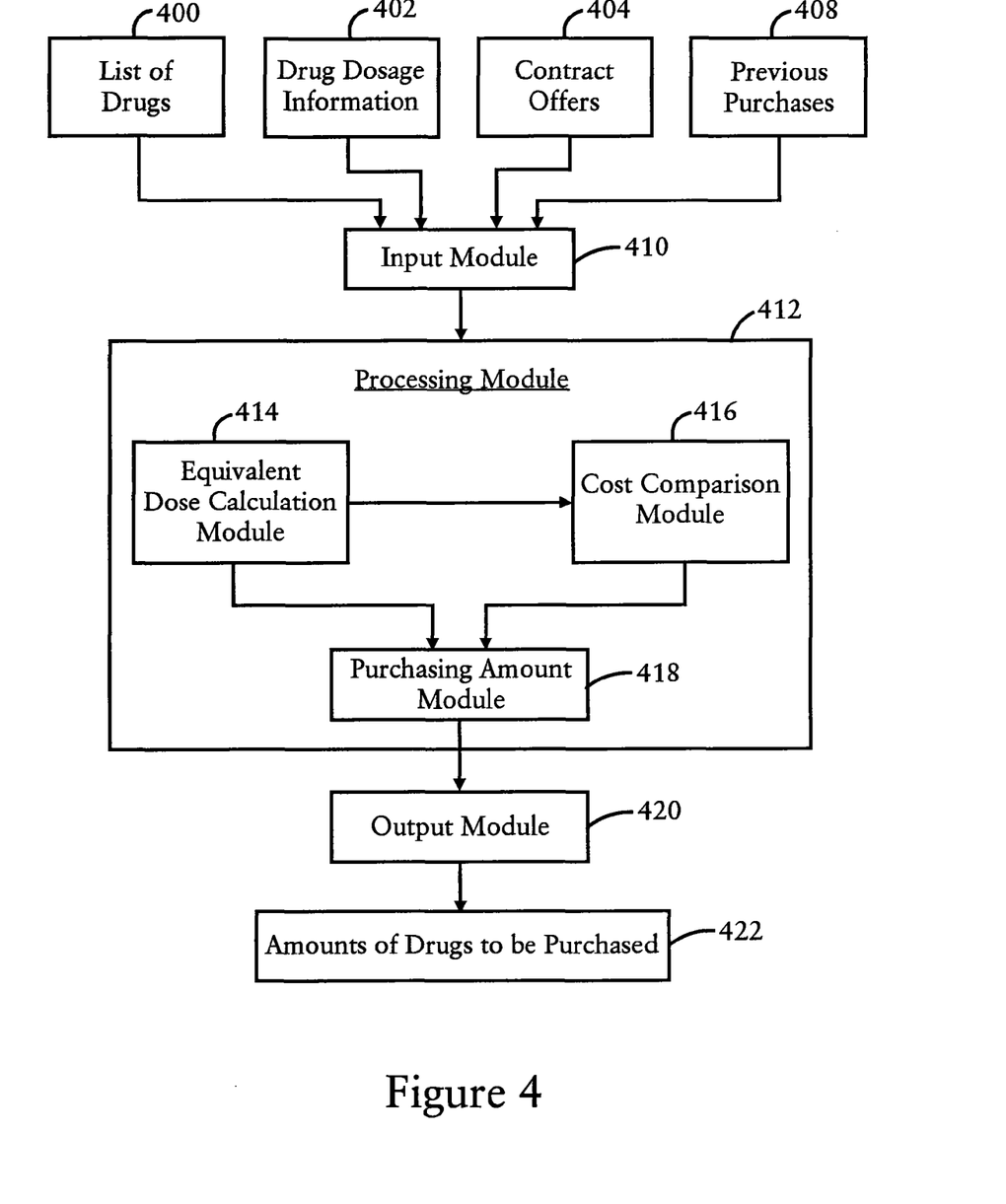
FIG. 4 is a block diagram depicting a system according to certain embodiments of the present disclosure for determining the amount of drugs to be purchased.

FIG. 2 shows a preferred method of the disclosure, and FIG. 4 depicts an exemplary architecture for performing the disclosed methods such an architecture may be realized by a computer a personal digital assistant, a networked computer, or any other suitable processing arrangement.

The first step 200, determines the equivalent doses between drugs used for the same purpose. Using the above example, the equivalent dose between drug 'X' and drug 'Y' would be: 2×3×3:1×2×4, or 9:4. The effectiveness, dose frequency and treatment period, as well as any other information necessary to determine the equivalent doses between drugs will be obtained from a source, such as the medical literature, the World Health Organization or the Food and Drug Administration, to name but a few. This and other information makes up the drug dosage information 402, which can be stored on a hard drive, a server, a database, obtained though a network, or acquired some other way. The determination of equivalent doses is performed by an equivalent dose calculation module 414.

The drug dosage information 402 can be entered into the system of FIG. 4 by obtaining the information from a hard drive, a server, a database, or a network, among other ways. The task of the input module 410 is to facilitate the input of information. The input module 410 may be a computer, a modem or a chip, etc., depending on how the input information 400, 402, 404 and 408 is stored and obtained. The input information includes a list of drugs 408, drug dosage information 402, contract offers 404 and previous purchases 408.

The list of drugs 400 may be entered in the same way as the drug dosage information 402. The list of drugs 400 will contain at least one list of different drugs which are used for the same purpose.

The current purchasing amounts of the organization i.e., the user, is received in step 202. Users may be hospitals, clinics, or pharmacies, among other entities. This review involves examining the user's previous purchases 403 to determine the user's current needs. A user's previous purchases 403 may contain purchases of drugs made over a past period, be it in years, months, weeks or days. FIG. 6 shows an example of the type of information that may make up a list of a user's previous purchases 403. The "Units" column 606 shows the number of units of the drug purchased, and the "Dollars" column 608 shows the total amount the user paid for the units. The list also contains other information, such as the national drug code, in the "NDC" column 602, and the strength of the drug in the "Strength" column 604. These are only some of the types of information which may appear in a user's list of previous purchases 403.

A user's previous purchases 403 can be stored on a hard drive, a server, a database, or a network, among other things. The previous purchases 403 can be entered into the system of FIG. 4 in the same way as the list of drugs 400 is entered—by reading the information from a hard drive, a server, a database, or a network, among other things.

Step 202 involves, among other things, organizing the user's previous drug purchases 408 into groups of drugs known as baskets, with each basket containing drugs that are used for the same purpose. The previous purchases 408 are also reviewed to determine how many equivalent units of each drug were purchased, using the equivalent doses calculated in the first step 200. These tasks, are performed by the equivalent dose calculation module 414 in the disclosed embodiments.

The third step 204 compares the costs of drugs according to equivalent doses. This involves adjusting the costs of drugs based on the available contract offers 404 from drug manufacturers, which will first be discussed. The cost comparison module 416 performs the cost comparison.

Figure 7:
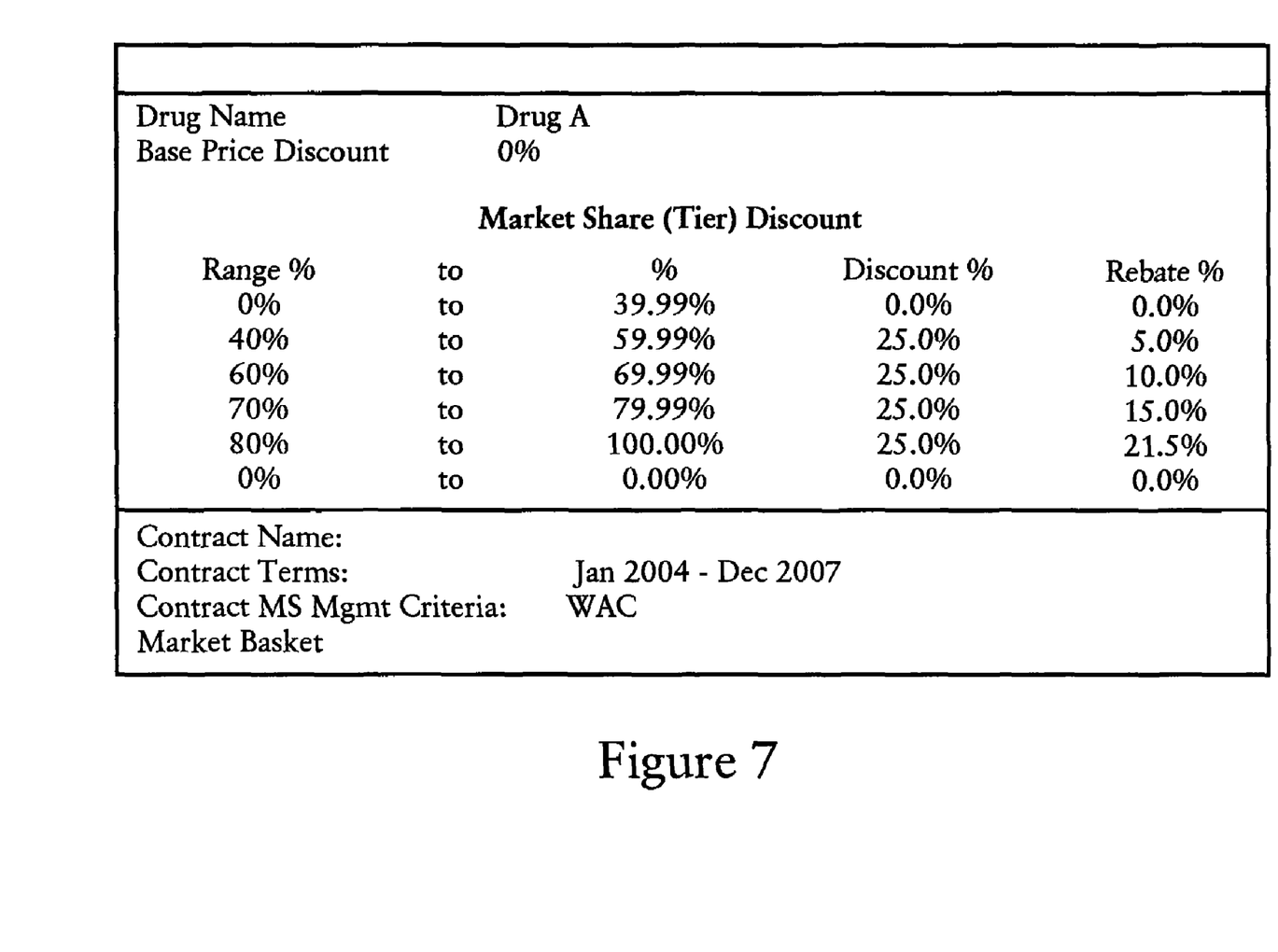
FIG. 7 is a table showing discounts and rebates of an exemplary contract offer.

The contract offers 404 will contain, among other things, information about discounts and rebates that various drug manufacturers are offering. FIG. 7 illustrates an example of the type of information that may be included in a contract offer 404. Here, the different "Market Share Ranges" (e.g., 0% to 39.99%) are referred to as tiers. The "Market Share Range" refers to the share of a market basket that is made up by purchases of a particular drug. So, if the basket consists of drugs that treat anemia, and a user's purchases of one particular anemia drug account for 60% of all of the user's anemia drug purchases, then the market share attributable to the drug is 60%. According to the contract offer in FIG. 7, if 60% of the user's purchases of drugs in that basket are from the offering drug manufacturer, the user would be entitled to a discount of 25% and a rebate of 10%. The user would be in the third tier. The top, or first tier is reserved for users purchasing within the 80% to 100% range, with the second tier being the 70% to 79.99% range etc. The higher the tier, the greater the discount and/or rebate will be. The difference between a discount and a rebate is that a discount is available immediately, whereas a rebate is only available once the user has purchased the required amount to qualify for the rebate. Thus, a user may sign a contract with a drug manufacturer to purchase 60% of its anemia drugs over a specific period, and will immediately receive a discount, but only receive a rebate at the end of the period if the user did in fact purchase 60% of its anemia drugs from the manufacturer.

The contract offers 404 can be stored on a hard drive, a server, a database, or a network, among other things. They 404 can be entered into the system of FIG. 4 by reading the information from a hard drive, a server, a database, or a network, among other things. As new contract offers become available, they can be entered into the system of FIG. 4. In certain embodiments of the present disclosure, the system of FIG. 4 may be connected to a network, server, or computer, among other things, which may enable the system to receive automatic periodic updates to contract offers as they become available.

The cost comparison module 416 adjusts the equivalent dose unit cost of the drugs according to the contract offers 404 (using the results from step 200), provided by the equivalent dose calculation module 414.

Suppose the following contract offer is available for drug 'X' in the earlier example:

| Tier | Market Share Range | Discount | Rebate |
|---|---|---|---|
| 3 | 0-39% | 0% | 0% |
| 2 | 40-79% | 20% | 5% |
| 1 | 80-100% | 25% | 10% |

Recall that in the described example the original cost of drug 'X' was $5, but that its equivalent dose cost per unit (in comparison to drug 'Y') was $1.61. The actual cost taking into account the discount and rebate in the offer above would be (assuming the rebate is calculated according to the original purchase price without the discount):

| Tier | Market Share Range | Discount | Rebate | Drug 'X' Cost |
|---|---|---|---|---|
| 3 | 0-39% | 0% | 0% | $1.61 |
| 2 | 40-79% | 20% | 5% | $1.21 |
| 1 | 80-100% | 25% | 10% | $1.05 |

Comparisons such as the one above may occur in numerous cases, including among previous purchases, desired purchases, or optimal purchases, which the present disclosure may determine according to various criteria. For example, an embodiment of the disclosure may calculate the least expensive alternative for an equivalent dose that meets a particular set of purchase amounts, or the user may fix certain purchase amounts, and then allow the embodiment to calculate the least expensive alternative for equivalent doses of the remaining purchases. Although the embodiment is able to compare any drug purchases, the ones mentioned are those most likely to be of interest to a user.

A fourth step 206, in the method is to determine the amounts of each drug to be purchased A purchasing amount module 418 performs step 406 in disclosed embodiments. Having compared the different costs of equivalent dose units of drugs according to the available offers in the previous step 204, the purchase amounts can be determined. This step 206 will be discussed in more detail with reference to FIG. 3.

In step 208, the amounts of the drugs to be purchased is output according to the decision of the previous step 206. The output module 420 outputs in step 422 a list of drug purchases determined in the previous step 206 including amounts of drugs to be purchased. The output module 420 may be a printer, a terminal, or a file, among other things.

Figure 3:
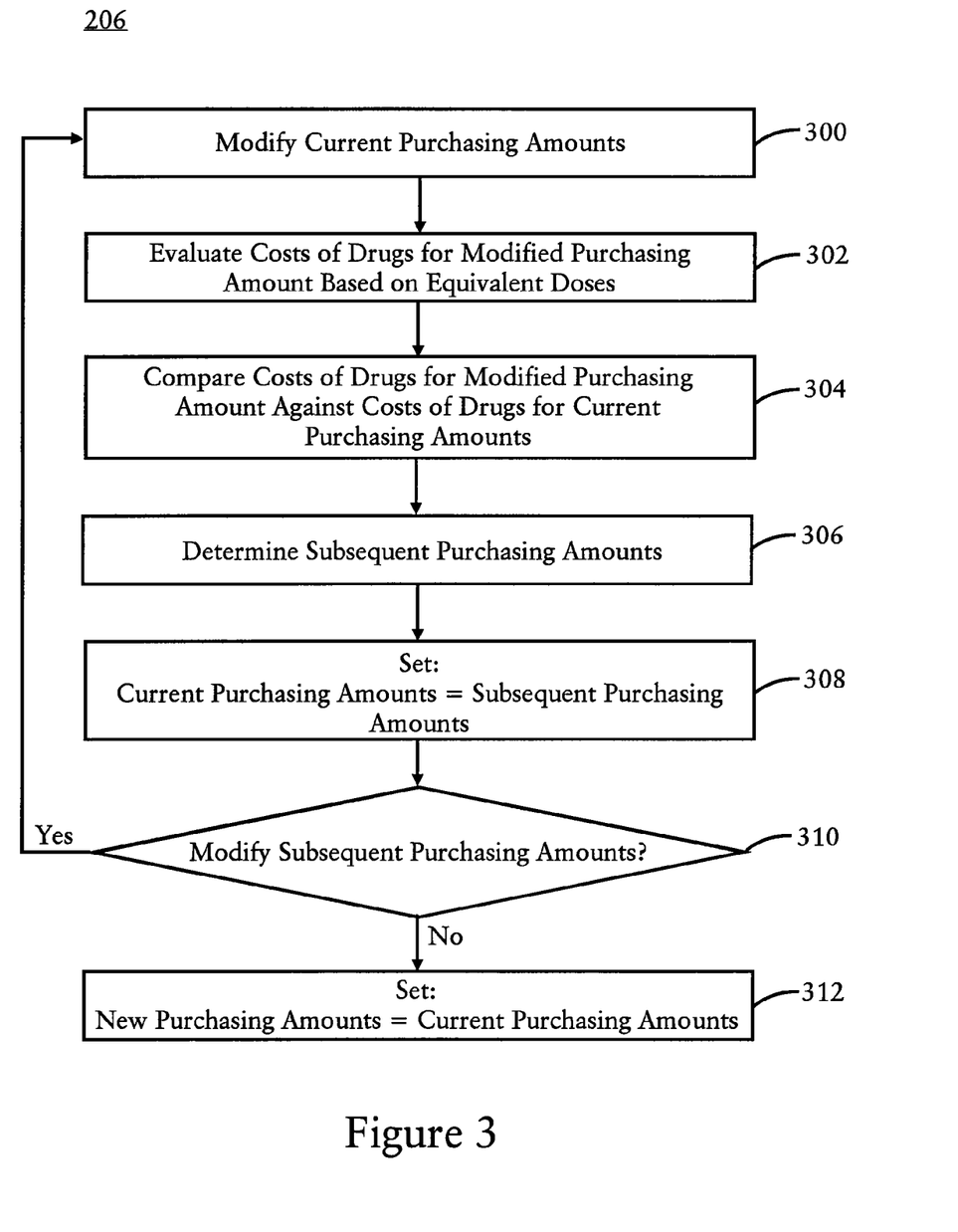
FIG. 3 is a flow chart diagram depicting the details of a step according to certain embodiments of the present disclosure for determining the amount of drugs to be purchased.
Figure 5:
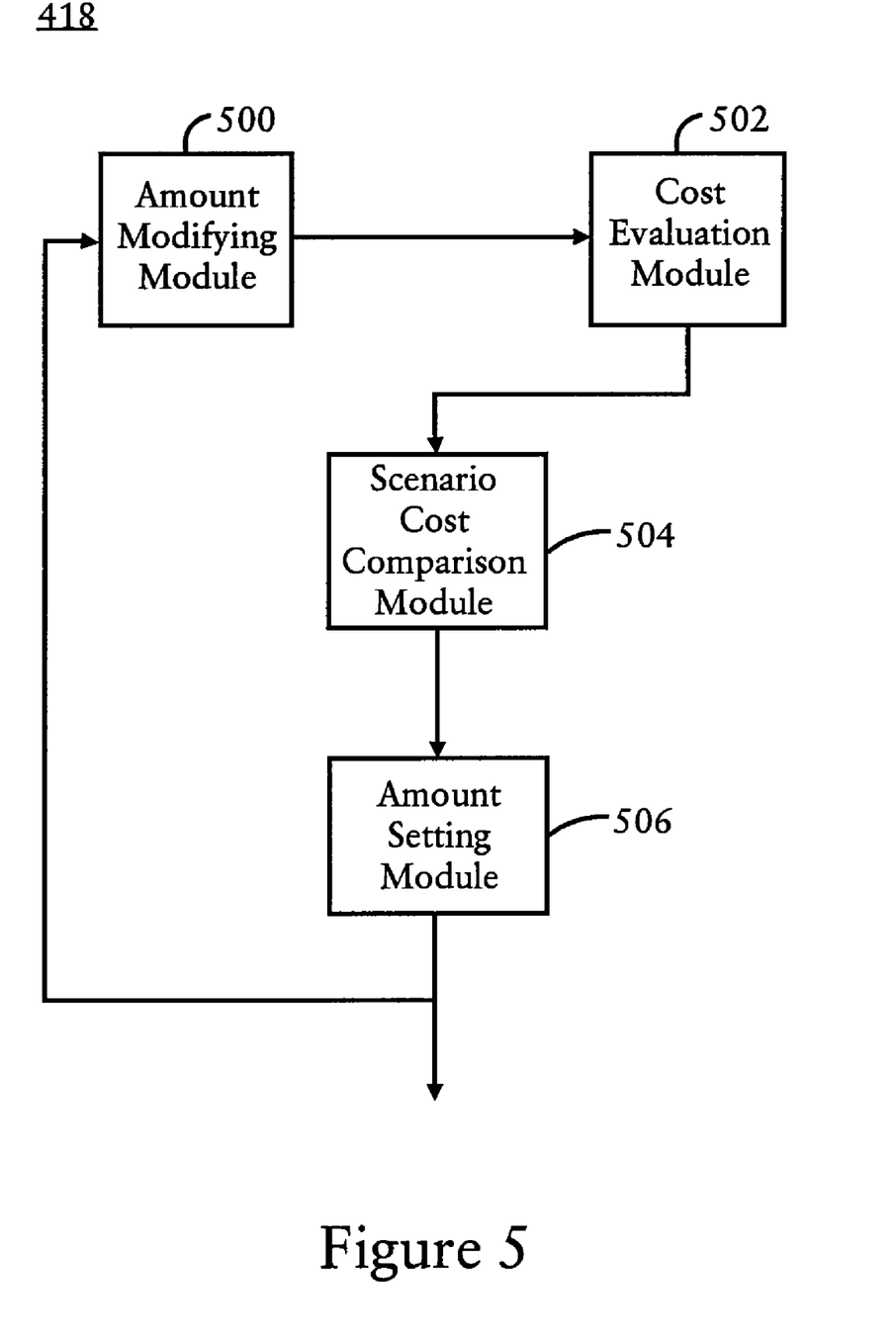
FIG. 5 is a block diagram depicting the details of one component of a system of the present disclosure for determining the amount of drugs to be purchased.

FIG. 3 shows an exemplary method for the step of determining the amounts of drugs to be purchased 206, and FIG. 5 shows a detailed view of the purchasing amount module 418 according to exemplary embodiments, which carries out step 206. Step 206 allows the user to modify drug purchasing amounts and compare the costs of the modified purchasing scenario to any other purchasing scenario of interest.

The step of determining new purchasing amounts 206 begins by allowing the user to modify the purchasing amounts of the drugs being considered 300. Employing an amount purchasing module 500, the user can modify the purchasing amount by ordinary units, by equivalent dose units, or by price, among other variables. In one embodiment the user is able to select an optimal modification, which allows the user to find the least expensive equivalent dose combination of drugs, among other things. The user may specify certain criteria in an optimal modification, such as requiring a minimum amount of a particular drug.

A cost evaluation module 502 then evaluates the cost of the modified purchasing amount based on equivalent dose units according to the available contract offers 402 in step 302. The costs of the modified purchasing amount scenario may then be compared to the costs of the original purchasing amount scenario, previous modified purchasing amount scenarios, or any other purchasing amount scenarios desired in step 304. This step is executed by the scenario cost comparison module 504.

Comparisons such as the one above may occur in numerous cases, including among previous purchase scenarios, desired purchase scenarios, or optimal purchase scenarios, which the present disclosure may generate according to various criteria. For example, an embodiment of the disclosure may calculate the least expensive alternative for an equivalent dose that meets a particular purchase scenario, or the user may fix certain purchases, and then allow the embodiment to calculate the least expensive alternative for equivalent doses of the remaining purchases. Although the embodiment is able to compare any drug purchase scenarios, the ones mentioned are those most likely to be of interest to a user.

In step 306, the user decides on the amounts of drugs to be purchased. The amount for review is set in step 308. This task is carried out by the amount setting module 506. The user is able to examine all the purchasing scenarios the user has generated, including scenarios for original purchasing amounts, modified purchasing amounts, and optimal purchasing amounts 504. The user may require the system to produce further information, such as incidental discounts which are available on unrelated drugs if a particular purchase is made. The user is then provided with in step 310 two options: (1) the user can decide on a particular purchasing scenario 312, and proceed to the next step of purchasing the drugs 208, or (2) the user may wish to generate further drug purchasing scenarios before making a final decision, in which case the user can return to the beginning of step 206 to set up the next purchasing scenario at step 300. The user may elect the second option as often as is necessary, or not at all. Once the user is finished generating purchasing scenarios, and is ready to make a purchase, the user selects the first option, and moves on from step 206 to step 208.

Figure 8:
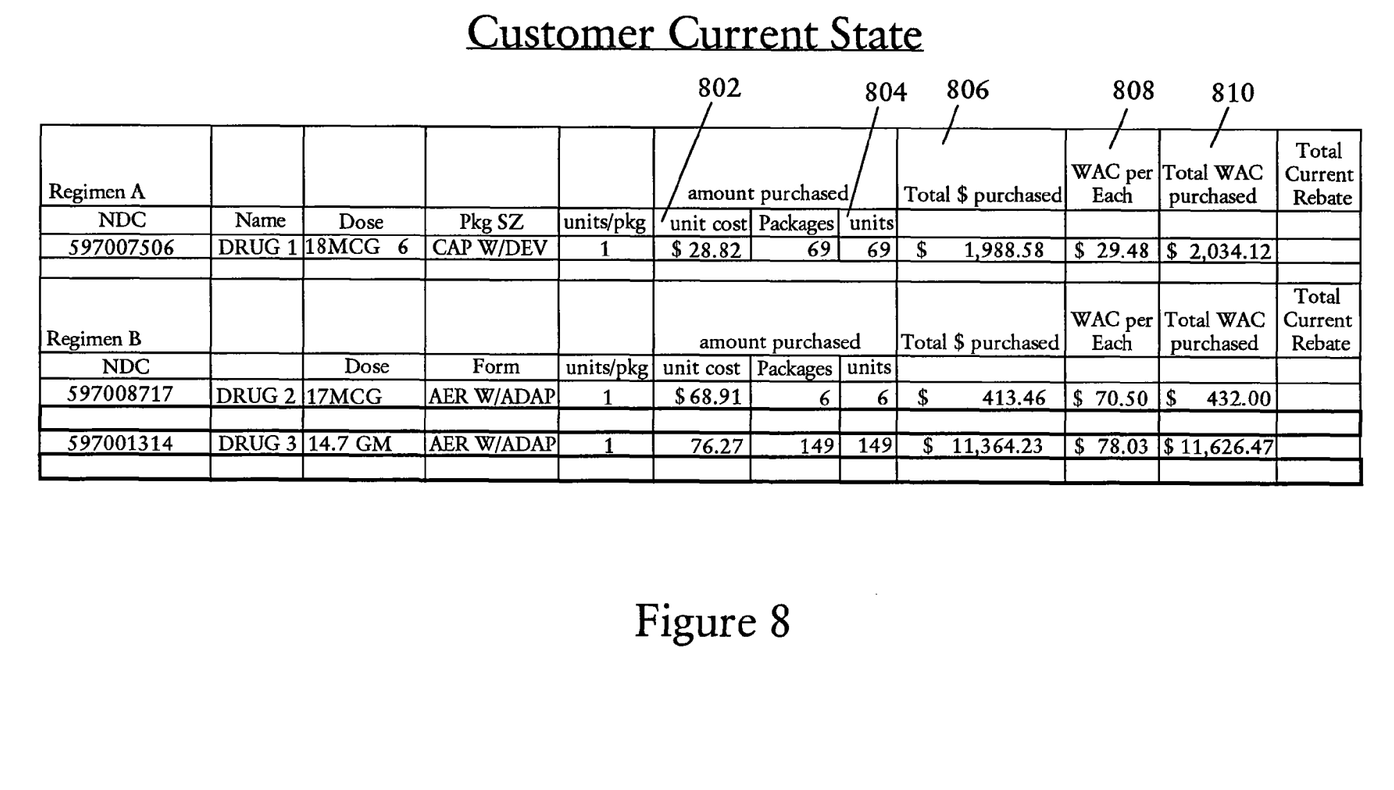
FIG. 8 is a table showing a user's exemplary previous drug purchases.

FIGS. 8 and 9 provide a more detailed example. FIG. 8 shows the user's previous purchases 408 of three drugs over the last year. The three drugs are in the same basket, and they are the only drugs in the basket for this user. They therefore define the market for this basket for this user. The "units" column 804 of FIG. 8 shows the number of units of the drug that the user purchased during the year. So, for example, the user purchased a total of 69 units of Drug 1 during the year. The "unit cost" column 802 shows the cost of one unit of a particular drug. The unit cost for Drug 1 is $28.82. The "Total $ purchased" column 806 of FIG. 8 gives the total amount that the user spent on a particular drug during the year. For Drug 1, the 69 units at $28.82 purchased during the year came to $1,988.58. In total, the user spent $13,766.23 on all the drugs in this basket during the year, which can be seen by summing the amounts in the "Total $ purchased" column 806.

WAC refers to "wholesale acquisition cost," which is the price of a drug as charged by the manufacturer, excluding any discounts and rebates. So the WAC of a drug is the price of a drug before taking into account discounts and rebates. The WAC is commonly used by manufacturers to determine the market share of a drug; other methods may include using dollar volume, equivalent units, or a combination of these and other variables. Market share is calculated by taking the total WAC for a particular drug, and dividing it by the total WAC for all of the different drugs in that drug's basket.

The "WAC per Each" column 808 lists the WAC per unit of a particular drug. So the WAC for a unit of Drug 1 is $29.48. The "Total WAC purchased" column 810 gives the total WAC amount that the user spent on a particular drug during the year. For the 69 units of Drug 1 purchased at a WAC of $29.48, the "Total WAC purchased" comes to $2,034.12. The difference between the WAC per unit, and the actual cost per unit is that the actual cost per unit takes into account any discounts that were available at the time of purchase. Thus, all WAC costs are higher than (or equal to) the actual costs.

For the purposes of the example in FIGS. 8 and 9, there are no discounts or rebates being offered.

The example of FIGS. 8 and 9 examines how two different purchasing scenarios (purchasing scenario 1 and purchasing scenario 2) compare to the current purchasing scenario. The current purchasing scenario is based on the user's past purchase amounts and assumes that the user will repeat these purchase amounts on the current occasion. Thus FIG. 8 not only gives shows the user's past purchases, but also the user's current purchasing scenario. FIG. 8 shows two equivalent dosage regimes: Regimen A, consisting of Drug 1, and Regimen B, consisting of Drug 2 and Drug 3. The Regimens are interchangeable, meaning that various combinations of Drugs 2 and 3 can be taken in place of Drug 1, and vice versa.

In scenario 1, the use of Drug 1 will be increased to 100%, and the use of Drugs 2 and 3 will be decreased to 0%. In scenario 2, the use of Drug 1 will be set to 80%, and the use of Drugs 2 and 3 will be set to 20%. Drug use is a measure of how the hospital actually uses the drug. According to the user's current purchasing scenario, as shown in FIG. 8, Drug 1 accounts for 31% of use, and Drugs 2 and 3 account for 69% of use.

FIG. 9 shows the comparison between purchasing scenarios 1 and 2, and the current purchasing scenario of the user according to the user's previous purchases, shown in FIG. 8. Purchasing scenario 1 is shown in the top half of FIG. 9, and purchasing scenario 2 is shown at the bottom. The information in FIG. 9 concerning the current purchasing scenario will be the same for both purchasing scenario 1 and purchasing scenario 2.

The column 902 displays the market share breakdown according to WACs. The user's total WAC for all the drugs in the basket is $14,084, shown in column 906 of FIG. 9 (for both purchasing scenarios 1 and 2). The total WAC is calculated by adding the WACs of the amounts of Drugs 1, 2 and 3, according to the current purchasing scenario, shown in FIG. 8. The WACs listed in FIG. 8 in the column titled "Total WAC purchased" 810 are: Drug 1—$2,034.12; Drug 2—$423.00; and Drug 3—$11,626.47, which when added, give the total WAC for all the drugs in the basket of $14,084.

The market share of Drug 1 is calculated as follows:

$$\text{Drug 1 Market Share} = \frac{\text{Total } WAC \text{ for Drug 1}}{\text{Total } WAC \text{ for All Drugs in Basket}}$$

$$= \frac{\$2,034.12}{\$14,084}$$

$$= 14\%$$

Similarly, for Drugs 2 and 3 the market share is calculated as follows:

$$\text{Drugs 2 \& 3 Market Share} = \frac{\text{Total } WAC \text{ for Drugs 2 \& 3}}{\text{Total } WAC \text{ for All Drugs in Basket}}$$

$$= \frac{\$12,049.47}{\$14,084}$$

$$= 86\%$$

The above market share breakdown is shown in FIG. 9, column 902, under the heading "Current EU spend" (for both purchasing scenarios 1 and 2).

In scenario 1, the percentage use breakdown is being modified from Drug 1=31% and Drugs 2 & 3=69%, to Drug 1=100% and Drugs 2 and 3=0%. This translates to a change in unit purchase as follows. Instead of purchasing 224 units of drugs in basket 1 with 69 units of Drug 1, 6 units of Drug 2 and 149 units of Drug 3, all 224 units purchased are of Drug 1. Thus, the total WAC for Drug 1 will be equal to the total WAC for all drugs in the basket, and the market share breakdown in purchasing scenario 1 will be Drug 1=100% of the market share, and Drugs 2 and 3=0%. This is shown in FIG. 9, column 902 for purchasing scenario 1, under the heading "Projected Market Share EU Dollars."

For purchasing scenario 2, the market share breakdown is not as simple. Here, the percentage use breakdown is Drug 1=80%, and Drugs 2 and 3=20%. For this usage pattern, the 224 units purchased must be apportioned as follows: 179 units of Drug 1, 8 units of Drug 2 and 37 units of Drug 3. To calculate the market share here, the WAC totals are first calculated. For Drug 1, the WAC per unit is $29.48 (recall from FIG. 8), and the total WAC for one hundred seventy-nine Drug 1 units is thus $5,276.92. For Drug 2, the WAC per unit is $70.50 (recall from FIG. 8), and the total WAC for eight Drug 2 units is thus $564.00. For Drug 3, the WAC per unit is $78.03 (recall from FIG. 8), and the total WAC for thirty-seven Drug 1 units is thus $2,897.10. So, the total WAC for all drugs in the basket in purchasing scenario 1 is $8,728.03. Drug 1 thus accounts for 60% of the market share, as $$\text{Drug 1 Market Share} = \frac{\text{Total WAC for Drug 1}}{\text{Total WAC for All Drugs in Basket}}$$
$$= \frac{\$5,276.92}{\$8,728.03}$$
$$= 60\%$$

and Drugs 2 and 3 account for the remaining 40%. This is shown in FIG. 9, column 902 for purchasing scenario 2, under the heading "Projected Market Share EU Dollars."

The "Current Spend" column 908 shows the total amount spent by the user on its previous purchases over the past year (which is confirmed by FIG. 8), because the user is presumed to be repeating the past purchases on the current occasion. As noted earlier, the user spent a total of $13,766.23 on all drugs in the basket, which can be seen in the "Current Spend" column 908 for both purchasing scenarios 1 and 2. The column 908 is referred to as the "Current Spend," because it shows how much the user is currently spending, and this is the primary figure with which the purchasing costs of scenarios 1 and 2 are being compared. The purchasing scenarios 1 and 2 are also being compared with each other.

The "Current Spend Net Estimated Rebate" column 910 shows the user's current total amount spent on previous purchases, less the anticipated rebate, according to the contracts which were in place at the time the user made its purchases. Here, no rebate is expected, so the "Current Spend Net Estimated Rebate" is equal to the "Current Spend" of $13,766.23, which can be seen in the "Current Spend Net Estimated Rebate" column 910 for both purchasing scenarios 1 and 2 in FIG. 9.

The "Generic" column 912 shows the total amount that the user would spend if the user had purchased generics available for Drugs 1, 2 and 3. In this example, there are no generic drugs available to replace Drug 1, 2 or 3, so the total cost listed in the "Generic" column 912 for both purchasing scenarios 1 and 2 matches the "Current Spend" amount of $13,766.23.

The "Projected EU" column 914 shows the equivalent dose cost of purchasing scenarios 1 and 2 excluding discounts and rebates. Recall that scenario 1 requires the purchase of two hundred twenty-four units of Drug 1, and no units of Drugs 2 and 3. The cost of 224 units of Drug 1 at $28.82 per unit (from the "unit cost" column 802 of FIG. 8) comes to $6,456, which can be seen under the "Projected EU" column 914 for scenario 1 in FIG. 9.

Purchasing scenario 2 requires the purchase of one unit of Drug 1, eight units of Drug 2 and thirty-seven units of Drug 3. The cost of units of Drug 1 at $28.82 per unit, eight units of Drug 2 at $68.91 per unit (from the "unit cost" column 802 of FIG. 8) and thirty-seven units of Drug 3 at $76.27 per unit (again from the "unit cost" column 802 of FIG. 8) comes to $8,532, which can be seen under the "Projected EU" column 914 for scenario 2 in FIG. 9.

The "Projected MS Disct" column 916 in FIG. 9 shows the discount that the user is entitled to based on market share. In the example, there is no discount available, so these entries are blank in both scenarios 1 and 2.

The "Projected Spend W/Discount" column 918 in FIG. 9 shows the user's projected cost less any discount, if the user follows scenario 1 or 2. In the example, there is no discount available, so in both scenarios 1 and 2, the entries in this column match the "Projected EU," for the respective purchasing scenario, which is the equivalent dose cost according to the respective purchasing scenario.

The "Projected Rebate" column 920 in FIG. 9 shows the rebate that the user is entitled to based on market share. In the example, there is no rebate available, so these entries are blank in both scenarios 1 and 2.

The "Projected Net Spend" column 922 in FIG. 9 shows the user's projected net cost less any discounts and rebates, if the user follows scenario 1 or 2. In the example, there are no discounts or rebates available, so in both scenarios 1 and 2, the first entry in this column matches the "Projected EU" for the respective purchasing scenario, which is the equivalent dose cost according to the respective purchasing scenario. For purchasing scenario 1, the user's "projected net spend" is $6,456. The cost of the user's current purchasing scenario, listed under the "Current Spend" column 908, is $13,766, which is $7,310 more than the projected net spend if the user follows purchasing scenario 1. Purchasing scenario 1 thus saves the user $7,310, which is indicated as the entry in parenthesis below the projected net spend amount.

For purchasing scenario 2, the user's "Projected Net Spend" is $8,532. The cost of the user's current purchasing scenario, listed under the "Current Spend" column 908, is $13,766, which is $5,234 more than the projected net spend if the user follows purchasing scenario 2. Purchasing scenario 2 thus saves the user $5,234, which is indicated as the entry in parenthesis below the projected net spend amount.

The user is free to create as many purchasing scenarios and comparisons as desired. It may modify a purchasing scenario based on the use of the drug, as in the example, or according to other factors including units, market share and total WAC, to name but a few. The user may also have the disclosed embodiment generate optimized alternatives such as minimizing units purchased, total WAC or market share of a drug.

The modules should in FIGS. 4 and 5 are depicted as separate. Such depiction is for explanatory purposes and ease of understanding. The various steps performed by the modules may be performed by a combined software embodiment provided on a computer readable medium, for example, to be performed by a single processor, or on multiple processors.

In summary, the present disclosure evaluates drug purchases according to available offers from drug manufacturers, based on the equivalent dosage regimens for similar drugs. The basic working of a preferred embodiment is as follows. The embodiment begins by determining equivalent doses for at least two drugs. Next, the purchasing amounts of the equivalent doses of the drugs are reviewed. The costs of the equivalent doses of the drugs are then compared, taking into account any contractual price adjustments, such as discounts and rebates. Following this, new purchasing amounts of the equivalent doses of the drugs are determined, using the results from the comparison in the previous step. Finally, the new purchasing amounts of the equivalent doses of the drugs are produced.

The description of the disclosure is provided to enable any person skilled in the art to practice the various embodiments described herein. While the present disclosure has been particularly described with reference to the various figures and embodiments, it should be understood that these are for illustration purposes only and should not be taken as limiting the scope of the disclosure.

There may be many other ways to implement the disclosure. Various methods and systems described herein may be partitioned differently from those shown without departing from the sprit and scope of the disclosure. Various modifications to these embodiments will be readily apparent to those skilled in the art, and generic principles defined herein may be applied to other embodiments. Thus, many changes and modifications may be made to the disclosure, by one having ordinary skill in the art, without departing from the spirit and scope of the disclosure.

In the previous detailed description, numerous specific details were set forth to provide a full understanding of the present disclosure. It will be obvious, however, to one ordinarily skilled in the art that the present disclosure may be practiced without some of these specific details. In other instances, well-known structures and techniques have not been shown in detail not to obscure the present disclosure.

What is claimed is:

1. A method comprising:
    obtaining drug information for each drug of at least two drugs, wherein the drug information comprises at least one of: drug strength, drug effectiveness, dosage frequency, and dosage period;
    determining, by an equivalent dose calculation module, equivalent doses between a first drug subset and a second drug subset of the at least two drugs by analyzing the drug information for each of the drugs of the at least two drugs, wherein the first drug subset and the second drug subset are equivalent dosage regimes;
    reviewing current relative purchasing amounts between the first drug subset and the second drug subset;
    comparing costs between the first drug subset and the second drug subset of the equivalent doses of the at least two drugs, wherein the comparing includes analyzing contractual price adjustments to the costs of the equivalent doses of the drugs based on the current relative purchasing amounts between the first drug subset and the second drug subset;
    determining, via a processing device, new relative purchasing amounts between the first drug subset and the second drug subset, based on the comparison; and
    outputting the new relative purchasing amounts.

2. The method of claim 1, wherein the step of determining new relative purchasing amounts of the equivalent doses of the drugs comprises:
    iteratively:
    a) modifying the current relative purchasing amounts of the equivalent doses of the drugs to obtain modified relative purchasing amounts of the equivalent doses of the drugs;
    b) comparing costs of the equivalent doses of the drugs, wherein the comparing includes analyzing contractual price adjustments to the costs of the equivalent doses of the drugs, based on the modified relative purchasing amounts of the equivalent doses of the drugs;
    c) comparing costs of the equivalent doses of the drugs based on the modified relative purchasing amounts of the equivalent doses of the drugs against costs of the equivalent doses of the drugs based on the current relative purchasing amounts of the equivalent doses of the drugs;
    d) determining subsequent relative purchasing amounts of the equivalent doses of the drugs, based on the step of comparing in step c;
    e) setting the current relative purchasing amounts of the equivalent doses of the drugs to be equal to the subsequent relative purchasing amounts of the equivalent doses of the drugs; and
    setting the new relative purchasing amounts of the equivalent doses of the drugs to be equal to the current relative purchasing amounts of the equivalent doses of the drugs.

3. The method of claim 1, wherein the contractual price adjustments are made according to available contract offers, which are stored in a database.

4. The method of claim 1, wherein the current relative purchasing amounts are set according to previous drug purchases of a user, the previous drug purchases being stored in a database.

5. The method of claim 1, wherein the step of comparing includes analyzing costs of generic drug equivalents.

6. The method of claim 1, further comprising automatically updating price adjustments based on new contract offers.

7. The method of claim 1, wherein the step of determining new relative purchasing amounts of the equivalent doses of the drugs comprises generating optimal purchasing amounts with respect to at least one of: lowest price, lowest market share and highest market share.

8. The method of claim 1, wherein the step of determining new relative purchasing amounts of the equivalent doses of the drugs comprises modifying at least one of: market share and drug use.

9. A computer readable medium, which when executed causes a computer to perform the steps comprising:
    obtaining drug information, for each drug of at least two drugs, wherein the drug information comprises at least one of: drug strength, drug effectiveness, dosage frequency, and dosage period;
    determining, by an equivalent dose calculation module, equivalent doses between a first drug subset and a second drug subset of the at least two drugs by analyzing the drug information for each of the drugs of the at least two drugs, wherein the first drug subset and the second drug subset are equivalent dosage regimes;
    reviewing current relative purchasing amounts between the first drug subset and the second drug subset;
    comparing costs between the first drug subset and the second drug subset of the equivalent doses of the at least two drugs, wherein the comparing includes analyzing contractual price adjustments to the costs of the equivalent doses of the drugs based on the current relative purchasing amounts between the first drug subset and the second drug subset;
    determining new relative purchasing amounts between the first drug subset and the second drug subset, based on the step of comparing; and
    outputting the new relative purchasing amounts.

10. The computer readable medium of claim 9, wherein the step of determining new relative purchasing amounts of the equivalent doses of the drugs comprises:
    iteratively:
    a) modifying the current relative purchasing amounts of the equivalent doses of the drugs to obtain modified relative purchasing amounts of the equivalent doses of the drugs;
    b) comparing costs of the equivalent doses of the drugs, wherein the comparing includes analyzing contractual price adjustments to the costs of the equivalent doses of the drugs, based on the modified relative purchasing amounts of the equivalent doses of the drugs;
    c) comparing costs of the equivalent doses of the drugs based on the modified relative purchasing amounts of the equivalent doses of the drugs against costs of the equivalent doses of the drugs based on the current relative purchasing amounts of the equivalent doses of the drugs;

d) determining subsequent relative purchasing amounts of the equivalent doses of the drugs, based on the step of comparing in step c;

e) setting the current relative purchasing amounts of the equivalent doses of the drugs to be equal to the subsequent relative purchasing amounts of the equivalent doses of the drugs; and setting the new relative purchasing amounts of the equivalent doses of the drugs to be equal to the current relative purchasing amounts of the equivalent doses of the drugs.

11. The computer readable medium of claim 9, wherein the contractual price adjustments are made according to available contract offers, which are stored in a database.

12. The computer readable medium of claim 9, wherein the current relative purchasing amounts are set according to previous drug purchases of a user, the previous drug purchases being stored in a database.

13. The computer readable medium of claim 9, wherein the step of comparing includes analyzing costs of generic drug equivalents.

14. The computer readable medium of claim 9, further comprising automatically updating price adjustments based on new contract offers.

15. The computer readable medium of claim 9, wherein the step of determining new relative purchasing amounts of the equivalent doses of the drugs comprises generating optimal purchasing amounts with respect to at least one of: lowest price, lowest market share and highest market share.

16. The computer readable medium of claim 9, wherein the step of determining new relative purchasing amounts of the equivalent doses of the drugs comprises modifying at least one of: market share and drug use.

17. A system for evaluating costs of drugs based on equivalent doses comprising:

an input module configured to receive input to the system, wherein the input includes drug information for each drug of at least two drugs, wherein the drug information comprises at least one of: drug strength, drug effectiveness, dosage frequency, and dosage period;

an equivalent dose calculation module configured to perform calculations according to equivalent doses between a first drug subset and a second drug subset of the at least two drugs by analyzing the drug information for each of the drugs of the at least two drugs, wherein the first drug subset and the second drug subset are equivalent dosage regimes;

a cost comparison module configured to compare costs between the first drug subset and the second drug subset of equivalent doses of the at least two drugs using the equivalent dose calculation module, wherein the comparing includes analyzing contractual price adjustments to the costs of the equivalent doses of the drugs based on current relative purchasing amounts between the first drug subset and the second drug subset;

a purchasing amount module configured to determine, via a processing device, new purchasing amounts between the first drug subset and the second drug subset, based on comparisons made by the cost comparison module; and an output module configured to output amounts of drugs to be purchased, wherein the output is stored in a database.

18. The system of claim 17, wherein the purchasing amount module comprises:

an amount modifying module configured to modify current relative purchasing amounts of equivalent doses of drugs;

a cost evaluation module configured to evaluate costs of modified relative purchasing amounts of equivalent doses of the drugs generated by the amount modifying module, and produce purchasing scenarios, wherein:

the evaluating includes analyzing contractual price adjustments to the costs of the equivalent doses of modified purchasing amounts of the drugs;

a purchasing scenario comprises amounts of equivalent doses of the drugs and costs of the amounts of equivalent doses of the drugs;

a scenario cost comparison module configured to compare purchasing scenarios produced by the cost evaluation module;

an amount setting module configured to set the current relative purchasing amounts of equivalent doses of the drugs to amounts of equivalent doses of the drugs in a purchasing scenario compared by the scenario cost comparison module.

19. The system of claim 17, wherein the contractual price adjustments are made according to available contract offers, which are stored in a database.

20. The system of claim 17, wherein the current relative purchasing amounts are set according to previous drug purchases of a user, the previous drug purchases being stored in a database.

21. The system of claim 17, wherein the cost comparison module is further configured to compare costs of equivalent doses of generic drug equivalents.

22. The system of claim 17, further comprising automatically updating price adjustments based on new contract offers.

23. The system of claim 17, wherein the purchasing amount module is further configured to determine new relative purchasing amounts of the equivalent doses of the drugs by generating optimal purchasing amounts with respect to at least one of: lowest price, lowest market share and highest market share.

24. The system of claim 17, wherein the wherein the purchasing amount module is further configured to determine new relative purchasing amounts by modifying at least one of: market share and drug use.

25. The method of claim 1, wherein the determining equivalent doses for the at least two drugs further comprises analyzing the drug strength, the drug effectiveness, the dosage frequency, and the dosage period for each drug of the two or more drugs to determine the equivalent dose for each of the drugs of the two or more drugs.

26. The computer readable radium of claim 9, wherein the step of determining equivalent doses for the at least two drugs further comprises analyzing the drug strength, the drug effectiveness, the dosage frequency, and the dosage period for each drug of the two or more drugs to determine the equivalent dose for each of the drugs of the two or more drugs.

27. The system of claim 17, wherein the equivalent does calculation module is further configured to perform calculations according to equivalent doses for the at least two drugs by analyzing the drug strength, the drug effectiveness, the dosage frequency, and the dosage period for each drug of the two or more drugs to determine the equivalent dose for each of the drugs of the two or more drugs.

* * * * *